US006922588B2

United States Patent
Kranz et al.

(10) Patent No.: US 6,922,588 B2
(45) Date of Patent: Jul. 26, 2005

(54) ELECTRODE LINE

(75) Inventors: Curt Kranz, Berlin (DE); Gernot Kolberg, Berlin (DE)

(73) Assignee: Biotronik Mess-und Therapiegeraete GmbH & Co., Berlin (DE)

( * ) Notice: Subject to any disclaimer, the term of this patent is extended or adjusted under 35 U.S.C. 154(b) by 147 days.

(21) Appl. No.: 10/417,399

(22) Filed: Apr. 16, 2003

(65) Prior Publication Data

US 2004/0102813 A1 May 27, 2004

(30) Foreign Application Priority Data

Apr. 16, 2002 (DE) .......................................... 102 17 828

(51) Int. Cl.⁷ ................................................ A61N 1/18
(52) U.S. Cl. ........................... 607/9; 607/119; 607/122
(58) Field of Search ............................... 607/9, 116, 119, 607/121, 122, 124

(56) References Cited

U.S. PATENT DOCUMENTS

| 5,433,730 A | 7/1995 | Alt | 607/5 |
| 5,476,496 A | 12/1995 | Strandberg | 607/122 |
| 5,554,176 A | 9/1996 | Maddison | 607/9 |
| 5,645,580 A | 7/1997 | Moaddeb | 607/122 |
| 5,681,514 A | 10/1997 | Woody | |
| 6,564,107 B1 * | 5/2003 | Bodner et al. | 607/122 |

* cited by examiner

Primary Examiner—Angela D. Sykes
Assistant Examiner—Alyssa M Alter
(74) Attorney, Agent, or Firm—Hahn Loeser & Parks LLP

(57) ABSTRACT

The invention concerns an electrode line (12) for an implantable intravascular electrostimulation device (10), wherein the electrode line (12) is electrically conductively connected with its proximal end (16) to the electrostimulation device (10) and with its distal end (18) to one or more functional elements. It is distinguished in that the electrode line (12) comprises an intrinsically conductive polymer in which the individual polymer chains of the polymer are so oriented that there is a high electrical conductivity in the axial direction of the electrode line (12) but not in the radial direction (electrical anisotropy).

20 Claims, 2 Drawing Sheets

ELECTRODE LINE

CROSS-REFERENCE TO RELATED APPLICATIONS

[Not Applicable]

STATEMENT REGARDING FEDERALLY SPONSORED RESEARCH OR DEVELOPMENT

[Not Applicable]

INCORPORATION BY REFERENCE

[Not Applicable]

1. Technical Field of the Invention

The present invention concerns an electrode line for an implantable intravascular electrostimulation device having the features recited in the appended claims.

2. Background of the Art

Electrode lines which for example are introduced into blood vessels or which lead through blood vessels into a chamber of a heart are fundamentally known. Such electrode lines generally carry electrodes which serve to electrically stimulate body tissue disposed therearound or to receive electrical signals. For example, stimulation electrodes for cardiac pacemakers are known.

Current cardiac pacemakers for that purpose include at least one pulse generator with a voltage source, the pulse generator being conductively connected by way of the electrode line to the electrodes which are connected to the tissue of the heart. Modern pulse and detection processes are generally based on multiple arrays of electrodes which are actuated simultaneously or in accordance with a predeterminable pattern. During stimulation or detection respectively, the polarity and the magnitude of the applied voltage frequency change drastically. Under some circumstances a part of the electrode lines can also be used for the actuation of sensors which detect physiological measurement values such as oxygen concentration, blood temperature and blood pressure. All those functional elements (electrodes, sensors) are usually connected to the cardiac pacemaker by way of metal conductors. However, electrode lines based on metal conductors are susceptible to fracture, which can give rise to problems in particular in connection with the steady contraction movement of the heart. In addition an increasing number of functional elements entails an increase in the diameter of the cable strand which is required for the supply of voltage to and actuation of the functional elements. Concomitantly therewith the stiffness of the electrode line is increased, which in turn has a detrimental effect in terms of implantation of the electrostimulation device and long-lasting compatibility thereof.

U.S. Pat. No. 5,476,496 to Standberg et al discloses an implantable electrode system which includes an indifferent electrode comprising an electrically conductive polymer. The electrode comprising the electrically conductive polymer is intended to provide a contact surface which is as large as possible, in relation to the tissue of the heart.

Maddison et al (U.S. Pat. No. 5,554,176) discloses electrode lines which can be used both for the supply of voltage to electrodes and also for the actuation of sensors. Inter alia coaxially extending regions of a conductive polymer, which are encased by an insulator, serve as electrical conductors. Those conductive regions of the electrode line can extend concentrically around the longitudinal axis of the electrode line or they comprise individual strands which are woven to each other or which extend in insulated relationship to the respective functional element. What is common to those arrangements is that electrically conductive and insulating regions alternate. That requires relative complex and thus cost-intensive manufacturing processes.

The object of the present invention is to provide an electrode line which is particularly simple to manufacture and which makes it possible to actuate a plurality of functional elements simultaneously or in a predeterminable manner.

SUMMARY OF THE INVENTION

That object is attained by an electrode line for an implantable intravascular electrostimulation device having the features recited in the appended claims. It is distinguished in that the electrode line comprises an intrinsically conductive polymer in which the individual polymer chains of the polymer are so oriented that there is a high level of electrical conductivity in the axial direction of the electrode line but not in the radial direction (electrical anisotropy). The electrode line is thus of a very substantially homogeneous structure in cross-section, which substantially simplifies manufacture.

Preferably polymers of polyacetylenes (PAC), polyparaphenylene (PPP), polyphenylene sulfide (PPS), polyparaphenylvinylene (PPV), polyphenylenebutadiene (PPB), polyparapyridine (PPYR), polypyrrole (PPY), polyfuran (PFU), polythiophen (PT), polyphenylamine (PANI), polyethylenedioxythiophen (PEDT), polyethylenedioxythiophen-polystyrene sulfonate (PEDT/PSS) and polyacene are preferably used as intrinsically conductive polymers. The materials are distinguished in that, under suitable polymerisation and processing conditions, they produce axially oriented polymer chains in the workpiece to be produced. A specific insulation resistance of an electrode line based on such an intrinsically conductive polymer is preferably in the radial direction greater than $5^{*-1}$ Ωm, in particular greater than 1 Ωm. Parallel to the longitudinal axis of the electrode line, that is to say in the axial direction, the specific insulation resistance of the electrode line is preferably between $10^{-2}$ and $10^{-6}$ Ωm, in particular between $10^{-4}$ and $10^{-6}$ Ωm. The anisotropic electrical conductivity of the materials is known per se so that there is no need for a detailed description here of that property and manufacture of the polymers.

It is further preferred that the electrode line is divided in its cross-section into individual sectors which are electrically conductive independently of each other in the axial direction. In that arrangement the sectors may preferably be in the form of peripheral segments or radial sectors of a circle. That can provide that, when an electrical voltage is applied, an electrical current flows only between the corresponding sectors at the proximal and distal ends of the electrode line.

The electrode line is further preferably encased by a biocompatible insulating sheath. Electrodes and sensors for determining physiological parameters are to be considered as functional elements which are to be contacted, in the distal region of the electrode line.

It has further proven to be advantageous if, at the proximal end of the electrode line, contact elements of the electrostimulation device are associated with one or more sectors. A contact element associated with a given sector or a plurality of sectors then guarantees in particular electrical contact with respect to the functional elements of the same sector or sectors, which elements are arranged at the distal end of the electrode line. It is accordingly possible to embody complex line geometries in a single electrode line.

Further preferred configurations of the invention are set forth by the other features recited in the appendant claims.

BRIEF DESCRIPTION OF THE DRAWINGS

The invention is described in greater detail hereinafter with reference to drawings in which.

DETAILED DESCRIPTION OF A PREFERRED EMBODIMENT

Figure 1:
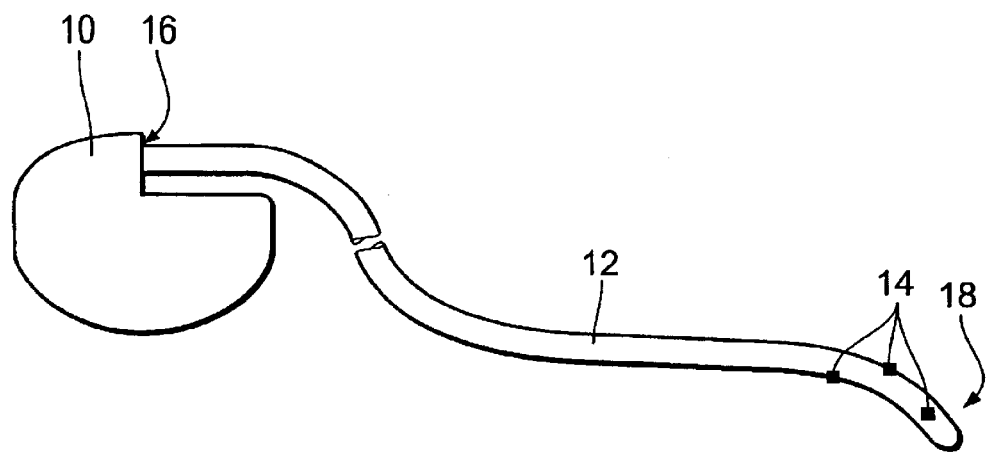
FIG. 1 is a view showing the principle of an electrostimulation device with electrode line.

FIG. 1 is a simplified view showing the structure in principle of an electrostimulation device 10 with an electrode line 12. The electrostimulation device 10, for example in the form of a cardiac pacemaker, includes inter alia components which serve as a voltage source, a control and evaluation unit and a telemetry unit. The structure in principle of electrostimulation devices of that kind has long been known. It is equally known for the electrostimulation device 10 to be implanted in intravascular tissue.

The electrode line 12 permits an electrical contact between the electrostimulation device 10 and a functional element 14 arranged at the distal end 18 of the electrode line. With its proximal end 16 the electrode line 12 communicates in a suitable fashion with the electrostimulation device 10. In this case the individual functional elements 14 can be in the form of electrodes for stimulating or sensing body tissue and/or they include sensors for determining physiological parameters. The latter can include for example blood pressure, blood temperature or oxygen partial pressure. What is common to the functional elements 14 is that they must be electrically conductively connected to the electrostimulation device 10 for performing the activities for which they are intended. The electrostimulation device 10 controls those activities of the functional elements 14 by means of its evaluation and control unit.

Actuation of the individual functional elements 14 by the electrostimulation device 10 can be effected simultaneously or in accordance with a predeterminable pattern. In regard to the details in that respect attention is directed to the extensive state of the art. It should just be noted at this point that the functional elements 14 as far as possible should be actuatable separately or at least in separate groups. For that purpose the electrode line 12 must have suitably differentiated, electrically conductive regions.

Figure 2:
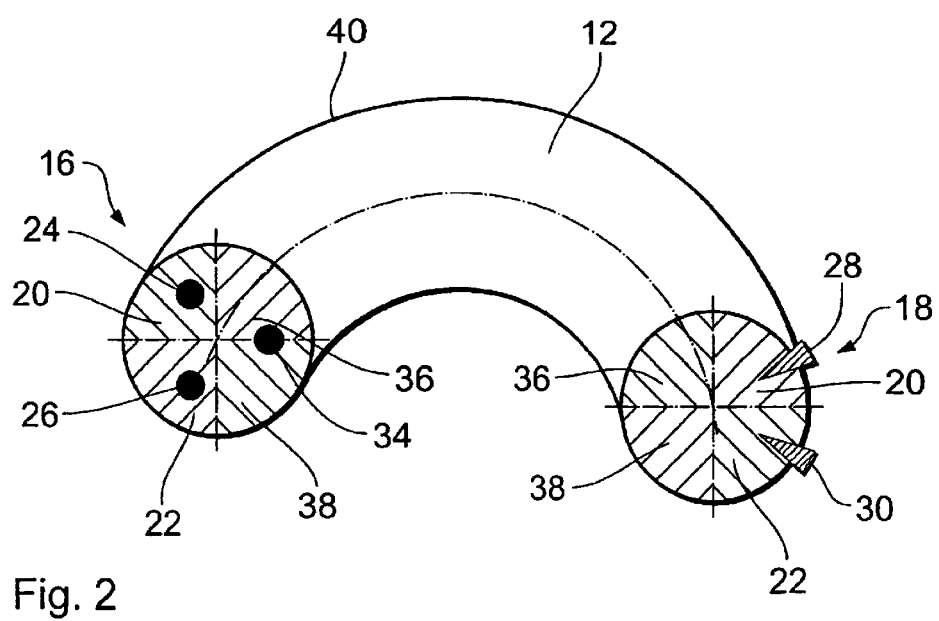
FIG. 2 shows the electrode line with cross-sections at its proximal and distal ends.

FIG. 2 shows the electrode line 12 with a cross-section at each of its proximal and distal ends 16 and 18. Provided at the distal end 18 as functional elements 14 are a first electrode 28 and a second electrode 30. In the region in which the proximal end 16 of the electrode line 12 comes into contact with the electrostimulation device 10, the electrode line has first and second contact elements 24, 26. The contact elements are connected to the voltage source and the evaluation and control unit respectively of the electrostimulation device 10, in a manner which is not shown but which is known per se. The first contact element 24 and the first electrode 28 are disposed in a common first sector 20 whose radial extent is indicated by the segment of a circle. The second contact element 26 and the second electrode 30 are correspondingly arranged in a second sector 22.

Besides the division, illustrated here, of the cross-section of the electrode line 12 into a total of four radial sectors of a circle, it is also possible to envisage configurations in which the sectors 20, 22 which are described in greater detail hereinafter form peripheral segments about a longitudinal axis of the electrode line 12. The sectors 20, 22 are based in each case on an intrinsically conductive polymer comprising polymer chains oriented predominantly in the axial direction.

Polymers of that kind generally have extended C=C-double bond systems which can be chemically easily attacked. That happens in the doping operation. An addition of electron donors (sodium, potassium, cesium) or electron acceptors ($I_2$, $SbCl_5$, $FeCl_3$ or similar) results in an increased degree of electron mobility and levels of conductivity of up to $10^5$ S/cm. Polymers of polyacetylenes (PAC), polyparaphenylene (PPP), polyphenylene sulfide (PPS), polyparaphenylvinylene (PPV), polyphenylenebutadiene (PPB), polyparapyridine (PPYR), polypyrrole (PPY), polyfuran (PFU), polythiophen (PT), polyphenylamine (PANI), polyethylenedioxythiophen (PEDT), polyethylenedioxythiophen-polystyrene sulfonate (PEDT/PSS) and polyacene have been found to be preferred as intrinsically conductive polymers. Suitable choice of the reaction conditions makes it possible to control polymerisation of the respective monomers used, in such a way that the resulting material exhibits an electrically anisotropic behaviour, when suitably processed. In that respect it is possible to have recourse to known plastic processing procedures. By presetting the respective polymerisation and processing conditions which are to be adapted to the respective individual case involved, it is possible to ensure that the individual polymer chains of the intrinsically conductive polymer are coaxially oriented in the longitudinal direction of the electrode line 12 and there is no conductivity worth mentioning in the radial direction.

Figure 3:
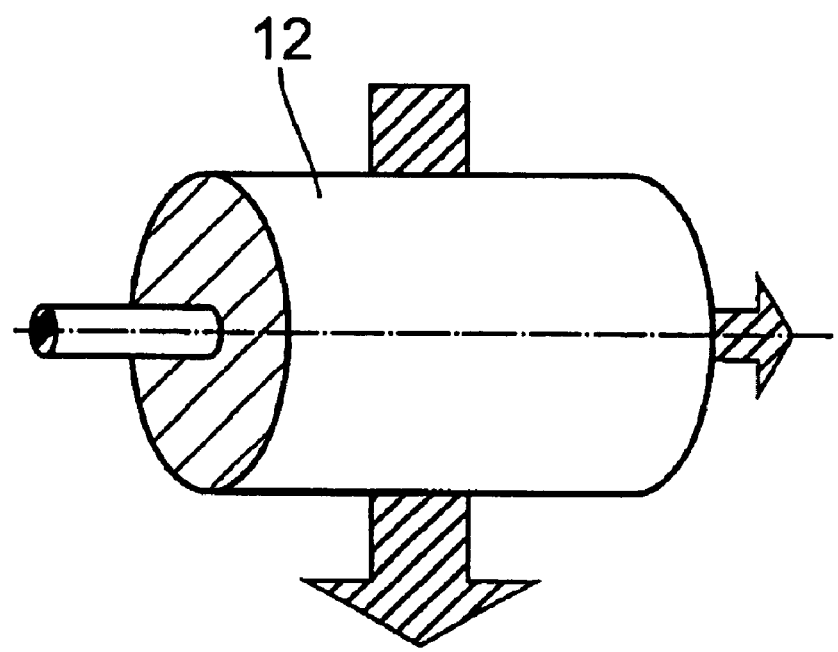
FIG. 3 is a diagrammatic illustration of the anisotropic electrical behaviour of the electrode line.

A specific insulation resistance of the electrode line 12 on the basis of such an intrinsically conductive polymer is in the radial direction greater than $5*10^{-1}$ Ωm and in an axial direction, that is to say in a direction extending parallel to the longitudinal axis of the electrode line 12, it is between $10^{-2}$ and $10^{-6}$ Ωm. The greater the differences between the axial and radial specific insulation resistances, the better is it possible to avoid incorrect connections. A particularly advantageous anisotropic electrical behaviour is afforded if the specific insulation resistance in the radial direction is greater than 1 Ωm and in the axial direction is between $10^{-4}$ and $1^{-6}$ Ωm. FIG. 3 is intended to illustrate once again the phenomenon of electrical anisotropy. The low axial specific insulation resistance is indicated by the narrow arrow extending parallel to the longitudinal axis of the electrode line 12. Disposed perpendicularly thereto is the large arrow representing a high level of specific insulation resistance.

By means of a suitable plastic processing procedure, it is possible for the electrode line 12 to be divided in respect of its cross-section into the sectors 20, 22 already mentioned above. The separate representation of the sectors 20, 22 means that it is possible effectively to prevent polymer chains extending over a plurality of sectors 20, 22. If now for example a voltage is applied to the first contact element 24, an electrical contact can be made only in relation to the first electrode 28 in the sector 20. If the second electrode 30 is to be actuated, contacting must accordingly be implemented by way of the second contact element 26 which is in the same sector 22.

It is also possible for a contact element at the proximal end 16 of the electrode line 12 to extend over a plurality of sectors and thus to permit the simultaneous actuation of a plurality of electrodes and/or sensors. An example in that respect is a contact element 34 which extends both over the sector 36 and also the sector 38. Functional elements—not shown here—which are in the region of the sectors 36, 38 can be simultaneously actuated in that manner.

The electrode line is preferably encased by an insulating sheath 40 to protect the intrinsically conductive polymer and to prevent indifferent creep leakage currents between the electrode line 12 and the adjoining tissue.

What is claimed is:

1. An electrode line for an implantable intravascular electrostimulation device, comprising:

a proximal end adapted to be electrically conductively connected to the electrostimulation device; and a distal end electrically conductively connected to at least one functional element, wherein the electrode line comprises an intrinsically conductive polymer exhibiting electrical anisotropy by having a high electrical conductivity in an axial direction of the electrode line and a low electrical conductivity in a radial direction of the electrode line.

2. The electrode line of claim 1, wherein:

the polymer is selected from the group consisting of: polyacetylenes (PAC), polyparaphenylene (PPP), polyphenylene sulfide (PPS), polyparaphenylvinylene (PPV), polyphenylenebutadiene (PPB), polyparapyridine (PPYR), polypyrrole (PPY), polyfuran (PFU), polythiophen (PT), polyphenylamine (PANI), polyethylenedioxythiophen (PEDT), polyethylenedioxythiophen-polystyrene sulfonate (PEDT/PSS), polyacene and combinations thereof.

3. The electrode line of claim 2 wherein:

a specific insulation resistance of the electrode line in the axial direction is between $10^{-2}$ and $10^{-6}$ $\Omega$m.

4. The electrode line of claim 3, wherein:

the specific insulation resistance in the axial direction is between $10^{-4}$ and $10^{-6}$ $\Omega$m.

5. The electrode line of claim 3, wherein:

a specific insulation resistance of the electrode line in the radial direction is greater than $5 \times 10^{-1}$ 106 m.

6. The electrode line of claim 5, wherein:

a specific insulation resistance of the electrode line in the radial direction is greater than 1 $\Omega$m.

7. The electrode line of claim 5, wherein:

said at least one functional element is an electrode for stimulating or sensing body tissue.

8. The electrode line of claim 7, wherein:

a cross section of the electrode line is divided into individual sectors that are electrically conductive independently of each other in the axial direction.

9. The electrode line of claim 8, wherein:

the sectors are in the form of peripheral segments or radial sectors of a circle.

10. The electrode line of claim 9, further comprising:

a biocompatible insulating sheath that encases the electrode line.

11. The electrode line of claim 9, further comprising:

contact elements at the proximal end of the electrode line, adapted for connecting to the electrostimulation device, and being associated with one or more of said sectors.

12. The electrode line of claim 1, wherein:

said at least one functional element is a sensor for detecting physiological parameters.

13. The electrode line of claim 12, wherein:

a cross section of the electrode line is divided into individual sectors that are electrically conductive independently of each other in the axial direction.

14. The electrode line of claim 13, wherein:

the sectors are in the form of peripheral segments or radial sectors of a circle.

15. The electrode line of claim 14, further comprising:

a biocompatible insulating sheath that encases the electrode line.

16. The electrode line of claim 14, further comprising:

contact elements at the proximal end of the electrode line, adapted for connecting to the electrostimulation device, and being associated with one or more of said sectors.

17. The electrode line of claim 16, wherein:

at least one said contact element associated with one or more of said sectors ensures electrical contact with respect to one or more of said at least one functional element of the same sector or sectors at the distal end of the electrode line.

18. The electrode line of claim 1, wherein:

a specific insulation resistance of the electrode line in the axial direction is between $10^{-2}$ and $10^{-6}$ $\Omega$m.

19. The electrode line of claim 18, wherein:

the specific insulation resistance in the axial direction is between $10^{-4}$ and $10^{-6}$ $\Omega$m.

20. The electrode line of claim 1, further comprising:

a biocompatible insulating sheath that encases the electrode line.

* * * * *